United States Patent
Ma

(10) Patent No.: US 10,822,293 B2
(45) Date of Patent: Nov. 3, 2020

(54) PROCESS FOR PRODUCING 1,2-PROPANEDIOL FROM GLYCEROL

(71) Applicant: Archer Daniels Midland Company, Decatur, IL (US)

(72) Inventor: Chi Cheng Ma, Champaign, IL (US)

(73) Assignee: ARCHER DANIELS MIDLAND COMPANY, Decatur, IL (US)

( * ) Notice: Subject to any disclaimer, the term of this patent is extended or adjusted under 35 U.S.C. 154(b) by 0 days.

(21) Appl. No.: 16/347,730

(22) PCT Filed: Nov. 6, 2017

(86) PCT No.: PCT/US2017/060187
§ 371 (c)(1),
(2) Date: May 6, 2019

(87) PCT Pub. No.: WO2018/093596
PCT Pub. Date: May 24, 2018

(65) Prior Publication Data
US 2019/0256447 A1 Aug. 22, 2019

Related U.S. Application Data

(60) Provisional application No. 62/422,835, filed on Nov. 16, 2016.

(51) Int. Cl.
*C07C 29/60* (2006.01)
*C07C 31/20* (2006.01)

(52) U.S. Cl.
CPC .......... *C07C 29/60* (2013.01); *C07C 31/205* (2013.01)

(58) Field of Classification Search
CPC ..................................................... C07C 29/60
See application file for complete search history.

(56) References Cited

U.S. PATENT DOCUMENTS

2010/0312023 A1 * 12/2010 Henkelmann .......... C07C 29/60
568/858

FOREIGN PATENT DOCUMENTS

WO WO-2009145691 A1 * 12/2009 ............. C07C 29/60

* cited by examiner

*Primary Examiner* — Medhanit W Bahta
(74) *Attorney, Agent, or Firm* — William B. Miller

(57) ABSTRACT

A process is described for producing biobased 1,2-propanediol, comprising reacting a glycerol-containing feed containing less than 5 weight percent of water with hydrogen in the presence of a catalyst, to partially convert glycerol in the glycerol containing feed to a crude reaction product mixture including 1,2-propanediol, removing 10 water from the crude reaction product mixture, recovering a portion but not all of the 1,2-propanediol from the crude reaction product mixture, and recycling the remainder of the 1,2-propanediol with unconverted glycerol and combining these with makeup glycerol to provide additional of the essentially anhydrous, glycerol-containing feed.

2 Claims, 1 Drawing Sheet

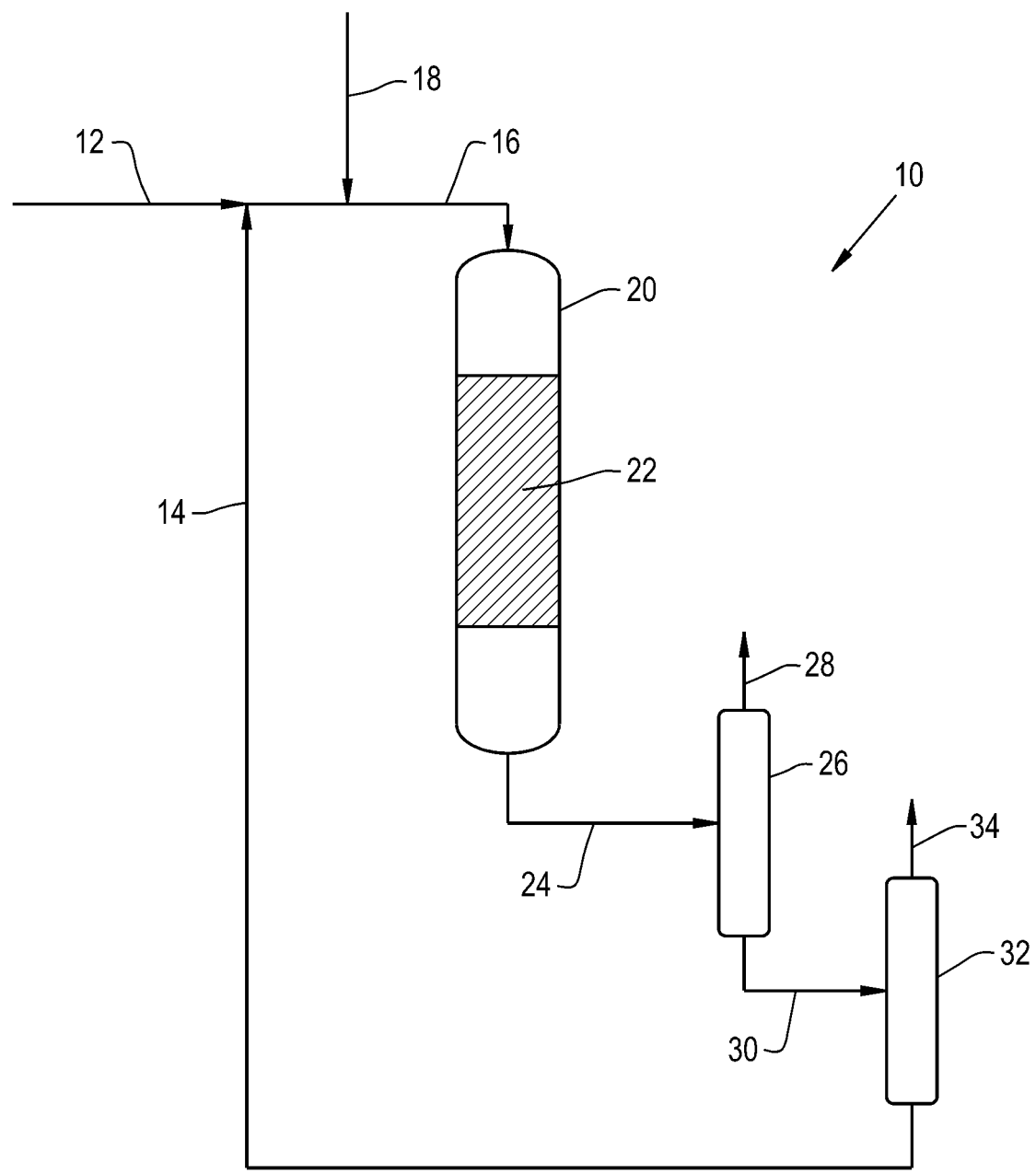

PROCESS FOR PRODUCING 1,2-PROPANEDIOL FROM GLYCEROL

The present application is a 371 National Phase Entry of International Patent Application PCT/US2017/060187 filed Nov. 6, 2017, which claims benefit of priority of U.S. Provisional Application No. 62/422,835 filed on Nov. 16, 2016, the contents of which are incorporated herein.

FIELD OF THE INVENTION

The present invention relates to processes for the manufacture of biobased 1,2-propanediol (hereafter, propylene glycol), and particularly to such processes for the manufacture of biobased propylene glycol from a glycerol-containing stream, especially a stream obtained from the production of biodiesel.

BACKGROUND

Fatty acid monoalkyl esters, especially methyl and ethyl esters, are presently produced and used for use as a biobased fuel in diesel engines. In the processing of biogenic oils and fats to provide the esters as a biodiesel fuel product, glycerol is also obtained as a co-product. One of known applications of the co-product glycerol is for making a biobased propylene glycol alternative to the propylene glycol commodity product that has historically been produced from non-renewable resources. A variety of hydrogenolysis methods and associated catalysts have in turn been developed to accomplish this conversion.

Certain of these methods and associated catalysts are described in U.S. Pat. No. 8,252,962 to Henkelmann et al. (hereafter, "Henkelmann"). As summarized in Henkelmann, for example, EP 0 523 015 is said to describe a process for preparing 1,2-propanediol and 1,2-ethanediol (ethylene glycol) in the presence of a Cu/Zn catalyst at a temperature of at least 200 degrees Celsius. The glycerol feed is in the form of an aqueous solution having a glycerol content of from 20 to 60 percent by weight, while the maximum glycerol content in the working examples is reported as 40 percent by weight.

WO 2005/095536 is said (in Henkelmann) to describe a low-pressure process for converting glycerol to propylene glycol, in which a glycerol-containing stream having a water content of at most 50 percent by weight is subjected to a catalytic hydrogenation at a temperature in the range of from 150 degrees Celsius to 250 degrees Celsius and a pressure in the range from 1 to 25 bar.

M. A. Dasari et al. are indicated by Henkelmann to describe, in Appl. Catalysis A: General 281, 2005, pp. 225-231, a process for low-pressure hydrogenation of glycerol to propylene glycol at a temperature of 200 degrees Celsius and a hydrogen pressure of 200 psi (13.79 bar) in the presence of a nickel, palladium, platinum, copper or copper chromite catalyst. Different reaction parameters were tested, including the water content of the glycerol used. Although the conversion increased with decreasing water content, the highest selectivity was achieved at a water content of 20 percent by weight.

Henkelmann summarizes U.S. Pat. No. 5,616,817 as describing a process for preparing 1,2-propanediol by catalytically hydrogenating glycerol at elevated temperature and elevated pressure, in which glycerol having a water content of at most 20 percent by weight is converted in the presence of a catalyst which comprises from 40% to 70% by weight of cobalt, if appropriate manganese and/or molybdenum and a small content of copper of from 10 to 20% by weight. The temperature is within a range of from about 180 to 270 degrees Celsius and the pressure within a range of from 100 to 700 bar, preferably from 200 to 325 bar.

Against the background of these prior art methods and associated catalysts, Henkelmann's process involves subjecting a glycerol-containing stream to a continuous hydrogenation in two hydrogenation reactors connected in series in the presence of a heterogeneous copper catalyst, with the conversion in the first reactor being at least 80%, based on the glycerol content. Suitable glycerol-containing streams according to Henkelmann are "in principle all glycerol-containing streams", col. 7, lines 52-53, though preferred glycerol-containing streams are characterized as having a water content of at most 30% by weight, preferably at most 20% by weight. Particular preference is given to a water content corresponding to glyceryl monohydrate (a water content of 16.3% by weight) or less. "Essentially anhydrous" glycerol, meaning glycerol with a water content of "at most 3% by weight, more preferably of at most 1% by weight" is contemplated (see col. 8, lines 5-6), as is the use of instead of water of a glycerol-miscible organic solvent (col. 8, lines 24-27), though neither are preferred. Henkelmann concludes in regard to the processing of glycerol-containing feeds having various water contents, as follows: "The hydrogenation of glycerol-containing streams, which are not essentially anhydrous and especially of streams which have a higher water content than glyceryl monohydrate is likewise possible with high yields and selectivities, but less economically viable owing to the reduced space time yields. Nevertheless, a water content in the range from 3 to 30% by weight may be advantageous for the rheological properties during the hydrogenation. A specific embodiment of the process according to the invention therefore relates to the use of glycerol-containing streams having a water content of from 3 to 30% by weight, preferably from 5 to 20% by weight, for reducing the viscosity in the hydrogenation."

According to col. 2, lines 2-43, the resultant "hydrogenation discharge" consisting essentially of 1,2-propanediol but further including methanol, ethanol, n-propanol, isopropanol, 1,3-propanediol, glycerol, ethylene glycol and water can be subsequently be worked up by customary processes known to those skilled in the art, for example, distillation, adsorption, ion exchange, membrane separation, crystallization, extraction or a combination of two or more of these. Henkelmann et al. teach that glycerol still present in the hydrogenation discharge "may, if appropriate after distillative removal," be recycled back for hydrogenation, and in fact the sole working example employed a glycerol-containing feed wherein pure glycerol was mixed with water in a mass ratio of glycerol to water of 9:1, and this feed was then combined with a recycle stream at a recycle ratio of 13:1 before the combination was fed into the hydrogenation reactor.

With a recited single-pass conversion in the main reactor of 93-94% (col. 22, lines 9-10), the hydrogenation discharge from this reactor would have contained in the range of 17% water just from the hydrogenolysis of glycerol. When accounting for the additional 10% of water already present in the glycerol-containing feed, the catalyst in the main reactor would in reality have been exposed to a significant amount of water in the optional ("may") glycerol recycle mode, on the order of 26 to 27 weight percent water.

WO 2009/145691 was not among the references cited by Henkelmann, but bears some similarity to Henkelmann in expressing a preference for what Henkelmann would characterize as an "essentially anhydrous" glycerol feed containing less than 3 percent of water. Water formed in the reaction is removed to "keep the water content in the obtained reaction solution at less than 5% by weight, such as 1.5% by weight", page 3, lines 13-14, and thereby avoid the water's being partly adsorbed on the copper-based catalyst's surface and inhibiting the "main reaction" as well as to avoid water's enhancing the decomposition of the catalyst structure and thereby causing decreased stability of the catalyst, page 3, lines 17-20. In one embodiment, the water is removed preferably by a countercurrent flow of hydrogen, which is said to remove water "assumed to be formed in the upper end" of a catalyst bed from continuing through the remainder of the bed, page 3, lines 27-28. In another embodiment, two or more catalyst beds are employed, and water is removed between the beds by a hydrogen gas flow passed through the reaction solution, while in still a third embodiment a combination of the countercurrent and between-bed flows of hydrogen are used. Recycle of the hydrogen after water removal is contemplated, as is the use in the alternative without recycle of an inert stripping gas such as nitrogen in place of the hydrogen. Recycle of unreacted glycerol is mentioned as well.

SUMMARY OF THE INVENTION

The following presents a simplified summary of the invention in order to provide a basic understanding of some of its aspects. This summary is not an extensive overview of the invention and is intended neither to identify key or critical elements of the invention nor to delineate its scope. The sole purpose of this summary is to present some concepts of the invention in a simplified form as a prelude to the more detailed description that is presented later.

With this understanding, the present invention in one aspect relates to a process for producing 1,2-propanediol wherein an essentially anhydrous glycerol-containing feed is combined with hydrogen in the presence of a hydrogenolysis catalyst under conditions effective to convert glycerol to a hydrogenolysis product mixture including 1,2-propanediol.

In one embodiment, the essentially anhydrous glycerol-containing feed consists essentially of a combination of glycerol and 1,2-propanediol.

In a further embodiment, the glycerol and 1,2-propanediol are obtained at least in part by removing water formed in the hydrogenolysis step from the hydrogenolysis product mixture and by partially separating 1,2-propanediol from unreacted glycerol, with recycling at least a part of the remaining combined 1,2-propanediol and glycerol to include in the essentially anhydrous glycerol-containing feed.

In one embodiment, the essentially anhydrous glycerol-containing feed consists essentially of from about 5 percent to about 50 percent by weight of glycerol, with the balance substantially being 1,2-propanediol.

In another embodiment, the essentially anhydrous glycerol-containing feed consists essentially of from about 10 percent to about 40 percent by weight of glycerol, with the balance substantially being 1,2-propanediol.

In another embodiment, the essentially anhydrous glycerol-containing feed consists essentially of from about 20 percent to about 30 percent by weight of glycerol, with the balance substantially being 1,2-propanediol.

In one embodiment, the hydrogenolysis catalyst is a heterogeneous copper-containing catalyst.

In a further embodiment, the heterogeneous copper-containing catalyst is a skeletal copper-based catalyst. The term "skeletal copper-based catalyst" as used herein means a porous catalytic alloy based material comprising copper and aluminum. The alloy in certain embodiments may further comprise small amounts of one or more additional metals added as promoters as further described hereafter, with common promoters including transition metals other than copper, for example, chromium, palladium, platinum, ruthenium, molybdenum, rhenium, manganese, nickel, zinc, zirconium, tungsten and combinations of two or more of these. When microscopically viewed as particulates, these high surface area, porous materials take on a skeletal appearance (sometimes also described as a "sponge like" appearance), having tortuous pore channels throughout. Skeletal copper catalysts of this character are well known, and have been manufactured and sold by W.R. Grace & Co. as part of a family of metal alloy derived products under the RANEY® trademark.

In one embodiment, the reaction is carried out at a temperature of less than about 250 degrees Celsius.

In another embodiment, the reaction is carried out at a temperature of less than about 230 degrees Celsius.

In another embodiment, the reaction is carried out at a temperature of less than about 215 degrees Celsius.

From a further perspective, the present invention relates in another aspect to a process for controlling the amounts of 1,2-propanediol and of 1,2-ethanediol produced relative to one another in the hydrogenolysis of a glycerol-containing feed, by controlling the amount of water in the glycerol-containing feed to less than 5 weight percent, preferably less than 3 weight percent, more preferably less than 2 weight percent, still more preferably less than 1 weight percent, and even more preferably less than 0.5 weight percent.

BRIEF DESCRIPTION OF THE DRAWING

FIG. 1 schematically illustrates an embodiment of a process according to the present invention.

DETAILED DESCRIPTION OF CERTAIN ILLUSTRATIVE EMBODIMENTS

The disclosures of all patent and non-patent literature referenced herein are hereby incorporated in their entireties.

As used in this application, the singular forms "a", "an" and "the" include plural references unless the context clearly indicates otherwise. The term "comprising" and its derivatives, as used herein, are similarly intended to be open ended terms that specify the presence of the stated features, elements, components, groups, integers, and/or steps, but do not exclude the presence of other unstated features, elements, components, groups, integers and/or steps. This understanding also applies to words having similar meanings, such as the terms "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers, and/or steps. The term "consisting essentially of", as used herein, is intended to specify the presence of the stated features, elements, components, groups, integers, and/or steps, as well as those that do not materially affect the basic and novel characteristic(s) of stated features, elements, components, groups, integers, and/or steps. Terms of degree such as "substantially", "about" and "approximately" as used herein mean a reasonable amount of deviation of the modified term (beyond that degree of deviation understood by the precision (significant figures) with which a quantity is expressed) such that the end result is not significantly changed. These terms of degree should be construed as including a deviation of at least plus or minus five (5) percent from the stated value, provided this deviation would not negate the meaning of the term modified.

Unless otherwise indicated, any definitions or embodiments described in this or in other sections are intended to be applicable to all embodiments and aspects of the subjects herein described for which they would be suitable according to the understanding of a person of ordinary skill in the art.

As indicated above, the present invention in one aspect relates to a process for producing 1,2-propanediol wherein an essentially anhydrous glycerol-containing feed is combined with hydrogen in the presence of a hydrogenolysis catalyst under conditions effective to convert glycerol to a hydrogenolysis product mixture including 1,2-propanediol. Henkelmann et al., as summarized previously, mention both the use of an "essentially anhydrous" glycerol-containing feed and the use of organic solvents "instead of" water, but still indicate that water should be preferred to the use of organic solvents and further teach that the glycerol-containing feed should contain at least 3% by weight of water, and preferably at least 5% by weight of water. Henkelmann et al. in this regard observe that "[t]he hydrogenation of glycerol-containing streams, which are not essentially anhydrous and especially of streams which have a higher water content than glyceryl monohydrate is likewise possible with high yields and selectivities, but less economically viable owing to the reduced space time yields," thus implying, if not expressly teaching, that were it not for the reduced productivity associated with inputting an inert such as water as a portion of the glycerol-containing feed, higher yields and selectivities would be realized with a feed comprised of greater than 16.3% by weight of water. In point of fact and as previously noted, in Henkelmann's only working example, Henkelmann et al. used a glycerol-containing feed with 10% water and by virtue of a recycle stream caused their catalyst to be exposed to considerably greater than 10% water.

We have now found, however, that the presence of even small amounts of water in a glycerol-containing feed (where term "glycerol-containing feed" as used herein shall be understood as referring to that material entering a hydrogenolysis reactor and being exposed to a hydrogenolysis catalyst therein, such material normally being comprised of both newly-supplied material as well as recycle material but being understood as also encompassing only newly-supplied material in the absence of a recycle loop) will be associated with the cleavage of carbon-carbon bonds in glycerol, and thus with the production of 1,2-ethanediol (ethylene glycol) as a co-product.

Of course, the production of ethylene glycol alongside propylene glycol may be desired, so that from another perspective, a process is enabled for producing both of ethylene glycol and propylene glycol, whereby the selectivity to one of these relative to the other in the hydrogenolysis of a glycerol-containing feed may be altered by selecting or modifying the amount of water in the glycerol-containing feed.

In the context of producing a biobased propylene glycol from a glycerol-containing feed, on the other hand, we prefer than an essentially anhydrous glycerol-containing feed is employed, where "essentially anhydrous" for our purposes will be understood as referring to a feed which contains less than 5 weight percent of water. Preferably, however, the feed will contain less than 3 weight percent, more preferably less than 2 weight percent, still more preferably less than 1 weight percent, and even more preferably less than 0.5 weight percent of water.

In one embodiment, the essentially anhydrous glycerol-containing feed consists essentially of a combination of glycerol and propylene glycol.

In a further embodiment, the glycerol and propylene glycol are obtained at least in part by removing water from the product mixture resulting from the hydrogenolysis of the glycerol-containing feed and by partially separating the desired propylene glycol product from unreacted glycerol, with recycling at least a part of the remaining combined propylene glycol and glycerol to include in the feed. The remainder of the essentially anhydrous glycerol-containing feed is in a preferred embodiment conventionally made up of a refined glycerol product, especially a USP grade glycerol product, which typically is at least about 99.5 to 99.7% pure glycerol with a corresponding maximum moisture content of 0.5% to 0.3% by weight.

In certain embodiments, the glycerol is from about 5, preferably from about 10, more preferably from about 20 percent by weight of the anhydrous glycerol-containing feed up to about 50, preferably up to about 40 and more preferably up to about 30 percent by weight of a combined glycerol/propylene glycol feed.

The hydrogenolysis catalyst can be any catalyst found useful in the presence of hydrogen for converting glycerol to propylene glycol, but a preferred catalyst is a heterogeneous copper-containing catalyst.

Such copper-containing catalysts have been extensively evaluated in many forms for use in this conversion, as have various noble metal-based catalysts. WO 2014/134733 to Dalal et al. is a recent example, and after reviewing a number of prior art methods involving both homogeneous and heterogeneous catalysts describes a process for the hydrogenolysis of glycerol to produce propylene glycol as the major product, which process comprises reacting the glycerol with hydrogen in the presence of a heterogeneous multicomponent catalyst based on Cu, Zn, Cr and Zr prepared by a co-precipitation method. The multicomponent catalyst was identified for further study after an initial screening of a number of catalysts in certain molar ratios, including Cu:Zn:Ni (3:2:2), Cu:Cr:Ni (3:1:2), Cu:Zn:Cr (3:2:1), Cu:Zn:Cr:Ni (3:2:1:2), Cu:Zn:Cr:Zr (3:4:1:3) and Cu:Zn:Cr:Zr (3:2:1:3).

Interestingly, while Dalal et al. reference prior publications by Chaminand et al. (*Green Chemistry*, 2004, vol. 6, pages 359-361) and Maris et al. (Journal of Catalysis, 2007, vol. 249, pp. 328-337) as support for Dalal's statement that "the Cu/ZnO based catalysts have been reported to give a high catalytic performance for the glycerol dehydroxylation reaction to propylene glycol under mild reaction conditions", on page 359 of Chaminand et al., a CuO—ZnO catalyst was initially selected for evaluation because of its efficiency in the hydrogenolysis of sorbitol to deoxyhexitols, but was found to have low activity and low conversion in glycerol hydrogenolysis (though it was observed to have high selectivity to propylene glycol consistent with the earlier findings of Montassier et al. (Montassier et al., Bulletin de la Societé Chimique de France 1989, No. 2, pp. 148-155) with a Raney copper catalyst).

Balaraju et al., "Selective Hydrogenolysis of Glycerol to 1,2-Propanediol Over Cu—ZnO Catalysts", Catal. Lett., vol. 126, pp. 119-124 (2008) report, however, "high conversion" with "highly selective" Cu—ZnO catalysts under certain conditions at a 50:50 weight ratio of copper to zinc and with small Cu and ZnO particles.

Copper-containing catalyst systems are addressed also in a series of patents assigned to BASF SE, see, e.g., U.S. Pat. Nos. 7,790,937, 8,252,962, 8,273,924 and 8,293,951 all to Henkelmann et al. In U.S. Pat. No. 8,293,951, after reviewing prior references employing various catalysts—Cr-activated copper or cobalt catalysts, nickel, copper-chromium-barium oxide, Raney copper, supported metal catalysts based on Cu, Pd and Rh, copper chromite, copper zinc oxide, copper aluminum oxide, copper silicon dioxide, platinum, cobalt/copper catalysts optionally containing manganese and/or molybdenum—a process is described employing at least three hydrogenation reactors in series with a heterogeneous copper catalyst. The copper catalyst is broadly described, and may additionally comprise at least one further element of "main group I, II, III, IV or V, of transition group I, II, IV, V, VI, VII or VIII and of the lanthanides (IUPAC Groups 1-15 and the lanthanides", col. 18, lines 26-30, though Raney copper and copper alloy-containing catalysts are preferred, particularly those whose metal component consists of copper to an extent of at least 95%, especially to an extent of 99%, col. 18, lines 32-39. Specific combinations of copper with other metals, in oxidic form, reduced elemental form or a combination are also listed, with certain combinations indicated as preferred: Cu (preferred); Cu,Ti (preferred); Cu, Zr; Cu, Mn; Cu, Al (preferred); Cu, Ni, Mn; Cu, Al, at least one further from La (preferred), W, Mo, Mn, Zn (preferred), Ti, Zr, Sn, Ni, Co; Cu, Zn, Zr (preferred); Cu, Cr, Ca; Cu, Cr, C (preferred); and Cu, Al, Mn (preferred) and Zr if appropriate. While very many combinations of other metals are thus indicated in this patent or are mentioned as known from the prior art, this particular patent contains but a single example, using a catalyst composed of the mixed oxides of Cu, Al and La.

A copper alloy-based sponge metal catalyst, especially, a RANEY® copper catalyst prepared from an alloy comprising copper and aluminum and optionally further comprising a promoter such as zinc, is especially preferred for use in the process of the present invention.

Preferably the hydrogenolysis is carried out under relatively mild temperature conditions to avoid yield losses through dehydration, for example, at a temperature of less than about 250 degrees Celsius, preferably of less than about 230 degrees Celsius, and still more preferably of less than about 215 degrees Celsius.

In an embodiment, the per-pass conversion of glycerol in the essentially anhydrous glycerol-containing feed is limited to less than full conversion to enable a combined glycerol/propylene glycol feed to be readily generated from the hydrogenolysis product mixture (e.g., by distillation and other conventional separation and purification methods), for example, controlling per-pass conversion of the glycerol at about 50 percent and less, preferably at about 40 percent and less and more preferably at about 30 percent and less.

Turning now to FIG. 1, an embodiment 10 of a process according to the present invention is illustrated, wherein a source 12 of makeup glycerol in propylene glycol is combined with a recycle stream 14 to provide an essentially anhydrous glycerol-containing feed 16 for feeding with hydrogen 18 to a hydrogenolysis reactor 20 containing a hydrogenolysis catalyst 22. The glycerol is partially converted therein to provide a hydrogenolysis product mixture 24 comprising unreacted glycerol and propylene glycol, as well as water and other alcohols. Preferably, the product mixture 24 consists substantially entirely of unreacted glycerol, propylene glycol and water, with less than about 1 percent by weight of other products. This product mixture 24 is distilled in a first, water removal column 26, with water and lighter alcohols such as methanol, ethanol, n-propanol and isopropanol being preferably entirely removed overhead in stream 28. The bottoms stream 30 from the water removal column 26, containing unconverted glycerol as well as propylene glycol as product from reactor 22 and diluent from streams 12 and 14, then proceeds to be distilled in a product recovery column 32. A saleable biobased propylene glycol product 34 is recovered overhead, while the bottoms are recycled back as recycle stream 14.

The present invention is more particularly illustrated by the following, non-limiting examples:

Example 1

A commercially-available RANEY® copper catalyst was loaded into a 30 cubic centimeter fixed bed reactor, and hydrogen was thereafter supplied to the reactor at a pressure of 1900 pounds per square inch, gauge, at 0.4 liters/minute, together with a solution of 28 percent by weight of glycerol in propylene glycol, resulting in a hydrogen:glycerol molar feed ratio of 17:1. The reactor temperature was maintained at 205 degrees Celsius, and the liquid hourly space velocity was 0.7 hr$^{-1}$. The product was collected over 48 hours' runtime and analyzed by liquid chromatography (LC). LC analysis showed about 92 percent by weight of 1,2-propanediol, about 6 weight percent of water and about 2 weight percent of glycerol in the product mixture, with no ethylene glycol being found (within detection limits) in the product.

Example 2

A propylene glycol product from which water and light alcohols had been removed as described above, comprised of 7 percent by weight of unreacted glycerol, 89 percent by weight of propylene glycol and 4 weight percent of water, was used to dilute glycerol and provide a feed again comprised of 28.1 weight percent of glycerol, with 68.7 percent by weight of propylene glycol and the balance (3.2 percent) of water. Hydrogen was again supplied at a pressure of 1900 pounds per square inch, gauge, at 0.4 liters/minute and at a hydrogen:glycerol molar feed ratio again of 17:1. Using the same reactor, catalyst, reaction temperature and LHSV as in Example 1, the product was determined by LC analysis to contain 87 weight percent of 1,2-propanediol and 4.8 weight percent of glycerol, with no ethylene glycol again being formed.

Example 3

For this example, a propylene glycol product from which water and light alcohols had been removed, comprised of 10 percent by weight of glycerol, 80 percent by weight of propylene glycol and 10 percent by weight of water was used to dilute glycerol and provide a feed of 28.1 weight percent of glycerol, 68.7 percent by weight of propylene glycol and 3.2 percent of water. Hydrogen was supplied at a pressure of 1900 pounds per square inch, gauge, at 0.4 liters/minute and at a hydrogen:glycerol molar feed ratio again of 17:1. Using the same reactor, catalyst, reaction temperature and LHSV as in previous Examples 1 and 2, the product was determined by LC analysis to contain 85 percent by weight of 1,2-propanediol and 7.4 weight percent of glycerol, but again with no formation of ethylene glycol.

Comparative Example 1

For purposes of comparison, a feed comprised of a comparable amount of water as exemplified in Henkelmann was prepared, containing 25 weight percent of water and 75 weight percent of glycerol. Using the same reactor and catalyst, at the same reaction temperature and LHSV, using the same source of hydrogen and same flow rate, with the same hydrogen:glycerol molar feed ratio (17:1), we found by LC that the product contained 33.2 percent by weight of 1,2-propanediol, 31.6 percent by weight of glycerol, 0.34 percent by weight of ethylene glycol and the balance of the water from the feed and from the hydrogenolysis reaction.

Comparative Example 2

For purposes of further comparison, a glycerol-containing feed was prepared which contained 50 weight percent of water and 50 weight percent of glycerol. Using the same reactor and catalyst, at the same reaction temperature and LHSV, using the same source of hydrogen and same flow rate, with the same hydrogen:glycerol molar feed ratio (17:1), we found by LC that the product contained 20.1 percent by weight of 1,2-propanediol, 26.2 percent by weight of unconverted glycerol, 0.32 percent by weight of ethylene glycol and the balance of the water from the feed plus that formed in the hydrogenolysis reaction.

What is claimed is:

1. In a process for producing 1,2-propanediol by reacting a glycerol-containing feed with hydrogen in the presence of a hydrogenolysis catalyst effective for catalyzing the reaction, the improvement comprising using a glycerol-containing feed containing less than 5 weight percent of water,
wherein the glycerol-containing feed consists of a product recycle portion from the hydrogenolysis process and a makeup portion of a virgin glycerol feed, and
wherein prior to the reacting, producing the glycerol-containing feed by steps comprising limiting the per-pass conversion of glycerol in the hydrogenolysis to less than full conversion, distilling off overhead substantially all of the water and lighter byproducts in the resultant product mixture in a first, water removal column, passing the bottoms from the first, water removal column to a product recovery column wherein a saleable propylene glycol product of at least 95 percent purity is recovered overhead and the bottoms is used as the product recycle portion from the hydrogenolysis process.

2. The process of claim 1, wherein the saleable propylene glycol product from the product recovery column is at least 99.5 percent pure.

* * * * *